Aug. 13, 1974 R. E. DANIELSON Plant Pat. 3,587
CHRYSANTHEMUM
Filed Aug. 16, 1972
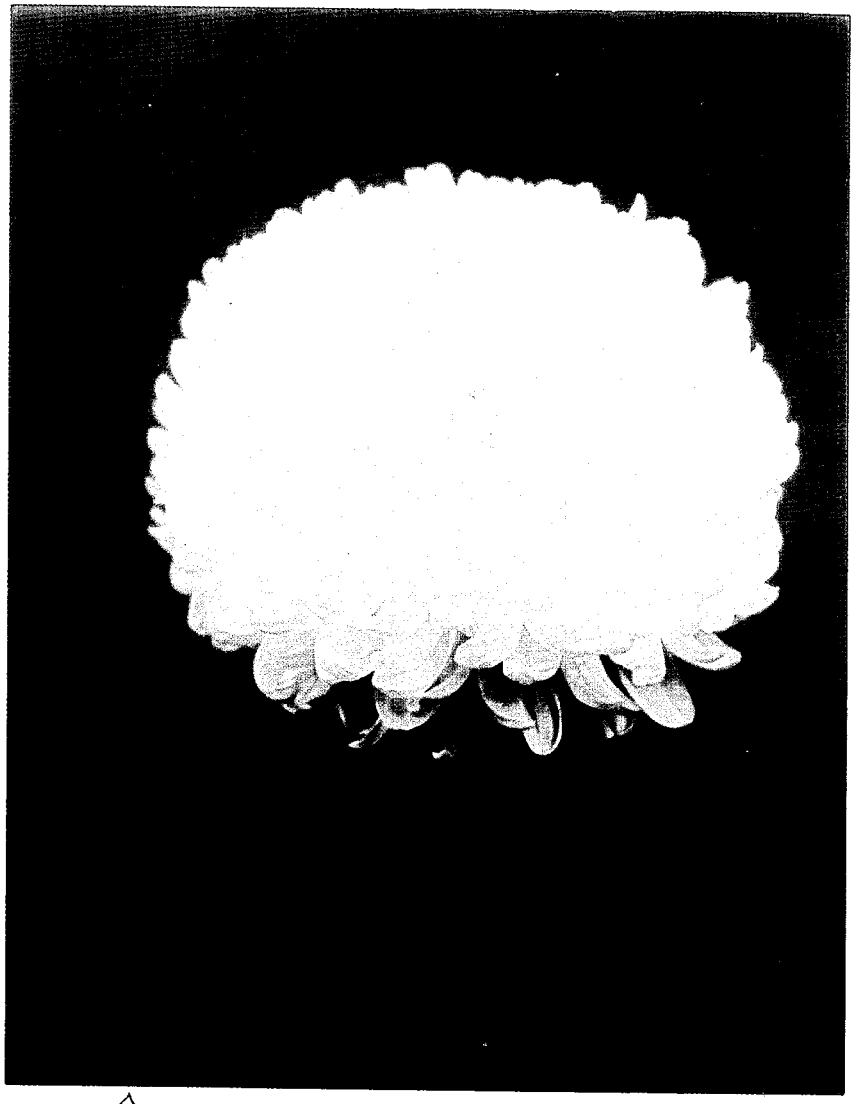
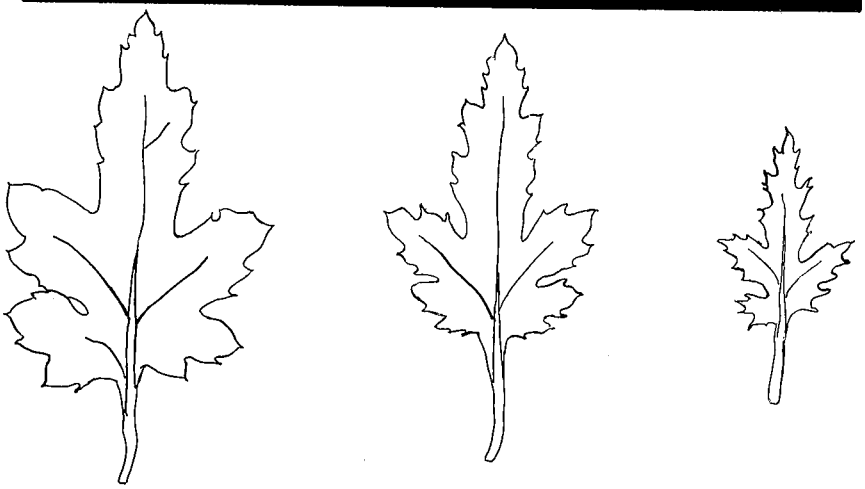

United States Patent Office

Plant Pat. 3,587
Patented Aug. 13, 1974

3,587
CHRYSANTHEMUM

Robert E. Danielson, West Chicago, Ill., assignor to Pan-American Plant Company, West Chicago, Ill.

Filed Aug. 16, 1972, Ser. No. 281,171
Int. Cl. A01h *5/00*
U.S. Cl. Plt.—78 1 Claim

ABSTRACT OF THE DISCLOSURE

A new and distinct variety of *Chrysanthemum morifolium* of the standard incurved type providing very large, well formed, globular blooms having an overall light yellow color, the central florets having a somewhat darker shade of yellow than the much larger mass of outer florets, this new variety being the first yellow mutation of the variety Dignity (Plant Pat. 3,309).

BACKGROUND OF THE NEW PLANT

This new variety of chrysanthemum plant was discovered by me in January 1970, at West Chicago, Ill., as a sport of the variety Dignity (Plant Pat. 3,309) produced by irradiation of the parent plant carried on with the objective of finding new and improved flower colors on plants having the advantageous characteristics of the original or parent variety. Asexual propagation of this sport, under my direction, at West Chicago, Ill., and subquent tests have shown this new variety to be as vigorous in growth habit as its parent and to have the same 9-week response with best growth during the high intensity sunlight periods of Spring, Summer and Fall. Asexual propagation of this new variety at West Chicago, Ill., and at Cortez, Fla., has demonstrated its color and growth characteristics to be firmly fixed and to hold true from generation to generation.

DESCRIPTION OF THE DRAWINGS

This new variety of chrysanthemum plant is illustrated by the accompanying drawing which shows the color characteristics of the flowers as nearly true as it is reasonably possible to obtain by conventional photographic procedures, and which shows by pen-and-ink drawings the distinctive configurations of typical specimens of the leaves.

DESCRIPTION OF THE NEW PLANT

The following is a detailed description of this new variety of chrysanthemum plant with color designations according to the Horticultural Color Chart by Robert F. Wilson and issued by the British Colour Council in collaboration with the Royal Horticultural Society.

*The Plant*

Origin: Sport
Parentage: Dignity, Plant Pat. 3,309, this sport being a mutation produced by irradiation.
Classification:
*Botanic.*—*Chrysanthemum morifolium.*
Commercial—Standard incurved.
Form: Perennial herbaceous bush.
Height: 2 to 4 feet.
Growth: Terminal. Vigorous, sturdy and upright with good strength.
Branching: Normal.
Foliage: Abundant with about 10 leaves per foot of stem length.
*Leaf size.*—Mature leaf—5½ inches long by 3½ inches wide.
*Shape.*—Lanceolate, lobed and somewhat serrated.
*Surface aspect.*—Glaucescent.

*Color.*—Upper side—Parsley Green 00962/1. Under side—Willow Green 000862.
*Venation.*—Pinnate.
*Petioles.*—1⅛ inches long.

*The bud*

Form: Globular—oval from side view and round from top view.
Size: ⅝ inch in diameter and ⅜ inch in depth, just before phyllaries open.
Opening rate: Bud opens slowly. Phyllaries begin to divide about two weeks from the time the bud becomes visible. Flowering occurs about four weeks later.
Color:
*When phyllaries first divide.*—Primrose Yellow 601/1.
*When florets begin to unfurl.*—Primrose Yellow 601.
Phyllaries: The outside of the receptacle bears many involucral bracts that are distinct. These bracts are spear shaped and stand up.
*Color.*—Inside—Scheeles Green 860/3. Outside—Scheeles Green 860/1.
*Surface aspect.*—Canescent.
Calyx: The calyx is represented by tiny bristles arising from the top of the ovary and occasionally it may be absent.
Peduncle: Length—½ inch.
Surface aspect: Canescent.

*The flower*

Blooming period: Can be flowered the year around with photoperiod control.
Response: 9-week.
Recommended flowering: Spring through Fall.
Natural season flowering: Early November.
Blooms: Flower type—incurved.
*Borne.*—A head of many florests on a single receptacle.
*Size.*—Very large; diameter 6½ inches, depth 5 inches.
*Shape.*—Flat and round when bloom first opens, becoming more globular as the flower matures.
*Florets.*—Very many with capitulum arrangement. Form: Linear with obtuse apex. Color: Outer florets—Primrose Yellow 601/3 with base of Uranium Green 63. Inside florets—Primrose Yellow 601/2. Reverse side of florets—Primrose Yellow 601/2.
Firmness: Medium.
Appearance: Velvety.
*Peduncle.*—½ inch long, sturdy and upright. Color: Scheeles Green 860/3.
Effect of weather: Florets become softer as seasons become warmer.
Persistence: Florets hang on and dry.
Lasting quality: 21 days on plant and 14 days as a cut flower.

*Reproductive organs*

Stamens: 5, syngenesious stamens, connate by their anthers to form a cylinder about the style.
*Filaments.*—¼ inch long and Light Yellow in color.
*Pollen.*—Yellow.
Pistils: One for each ray floret.
*Style.*—3/16 inch long.
*Stigmas.*—Yellow.
Ovaries: Inferior and bicarpellate.

This first yellow mutation of the variety Dignity (Plant Pat. 3,309) is particularly distinguished by its large, well formed, globular flower which exhibits a unique primrose yellow color. Otherwise this variety retains all of the advantageous and distinctive characteristics of the parent variety, Dignity, and is a very fine color companion to the parent both as potted plants and as cut flowers.

The claim:

1. A new and distinct variety of chrysanthemum plant substantially as herein shown and described, characterized by the unique light yellow color of the generally incurved florets of its very large globular flowers, and by its retention of the growth and response characteristics of its parent variety.

No references cited.

ROBERT E. BAGWILL, Primary Examiner